United States Patent
Kleinschrodt

(10) Patent No.: US 9,101,471 B2
(45) Date of Patent: Aug. 11, 2015

(54) SYSTEMS AND DELIVERY HANDLES FOR DELIVERING PROSTHETIC HEART VALVES DISPOSED ON VALVE HOLDERS

(75) Inventor: Holly Kleinschrodt, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 483 days.

(21) Appl. No.: 13/494,777

(22) Filed: Jun. 12, 2012

(65) Prior Publication Data

US 2012/0316639 A1 Dec. 13, 2012

Related U.S. Application Data

(60) Provisional application No. 61/496,206, filed on Jun. 13, 2011.

(51) Int. Cl.
*A61F 2/24* (2006.01)

(52) U.S. Cl.
CPC .............. *A61F 2/2427* (2013.01); *A61F 2/2439* (2013.01); *A61F 2/2466* (2013.01); *A61F 2220/0033* (2013.01); *A61F 2250/006* (2013.01)

(58) Field of Classification Search
CPC .... A61F 2/2427; A61F 2/2439; A61F 2/2466
See application file for complete search history.

(56) References Cited

U.S. PATENT DOCUMENTS

| | | | |
|---|---|---|---|
| 4,266,340 A | 5/1981 | Bowman | |
| 4,599,793 A | 7/1986 | Iten | |
| 5,350,420 A | 9/1994 | Cosgrove et al. | |
| 5,522,884 A | 6/1996 | Wright | |
| 5,669,919 A | 9/1997 | Sanders et al. | |
| 5,792,139 A | 8/1998 | Chambers et al. | |
| 5,822,869 A | 10/1998 | Metcalf et al. | |
| 5,843,177 A | 12/1998 | Vanney et al. | |
| 6,214,043 B1 * | 4/2001 | Krueger et al. | .............. 623/2.11 |
| 6,319,280 B1 | 11/2001 | Schoon | |
| 6,749,630 B2 | 6/2004 | McCarthy et al. | |
| 6,964,682 B2 | 11/2005 | Nguyen-Thien-Nhon et al. | |
| 7,476,247 B2 | 1/2009 | Ryan et al. | |

(Continued)

FOREIGN PATENT DOCUMENTS

WO 99/49816 A1 10/1999

OTHER PUBLICATIONS

International Search Report for corresponding international application No. PCT/US2012/042270 dated Jun. 13, 2012.

*Primary Examiner* — Jonathan W Miles
*Assistant Examiner* — Todd J Scherbel
(74) *Attorney, Agent, or Firm* — AnneMarie Kaiser; Guy Cumberbatch; Pui Tong Ho

(57) ABSTRACT

A system delivering a prosthetic heart valve includes a delivery handle, a heart valve, and a valve holder. The delivery handle includes a rod, a button, and a valve holder attachment interface, where the button is configured to move between a first position and a second position along an axial length of the rod, and the valve holder attachment interface is mechanically coupled to the button and configured to move between an engaged position and a disengaged position. The heart valve includes a prosthetic valve. The valve holder is connected to a proximal end of the heart valve and includes a boss, a holder ring, and a handle attachment interface. The holder ring includes the heart valve mounted thereto and is coupled to the boss, and the handle attachment interface is formed on the boss and is configured to receive and mate with the valve holder attachment interface.

16 Claims, 5 Drawing Sheets

(56) References Cited

U.S. PATENT DOCUMENTS

| | | |
|---|---|---|
| 7,575,595 B2 | 8/2009 | Ingle et al. |
| 7,658,763 B2 | 2/2010 | Stobie |
| 8,163,009 B2 | 4/2012 | Wright et al. |
| 2002/0133226 A1 | 9/2002 | Marquez et al. |
| 2006/0254398 A1 | 11/2006 | Ward |
| 2008/0262603 A1 | 10/2008 | Giaquinta et al. |
| 2011/0066232 A1* | 3/2011 | Riveron et al. ............ 623/2.11 |
| 2014/0114405 A1 | 4/2014 | Paul et al. |

* cited by examiner

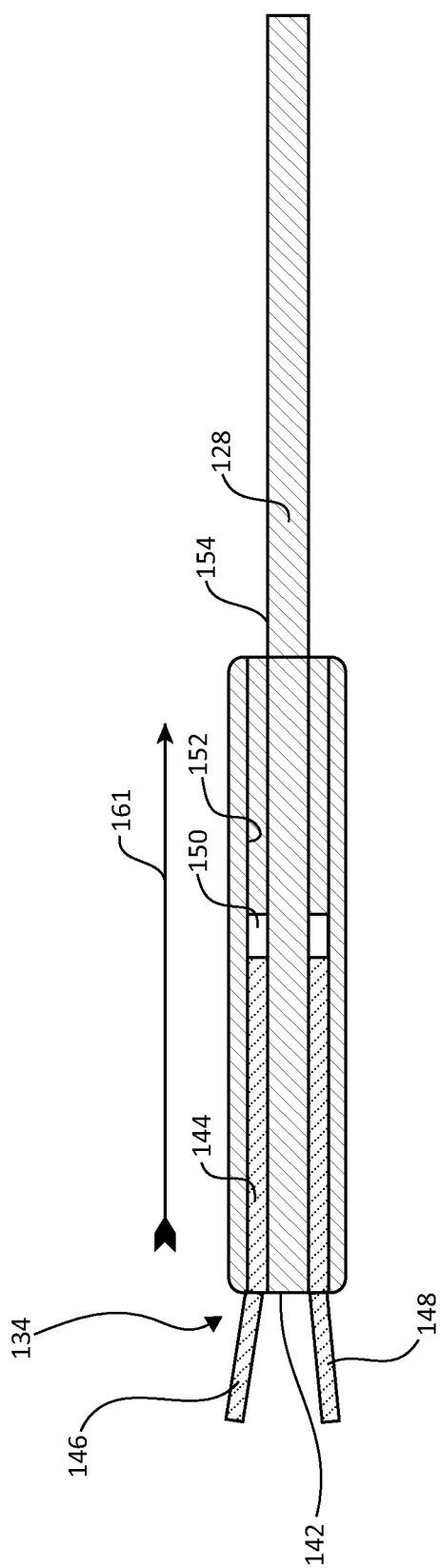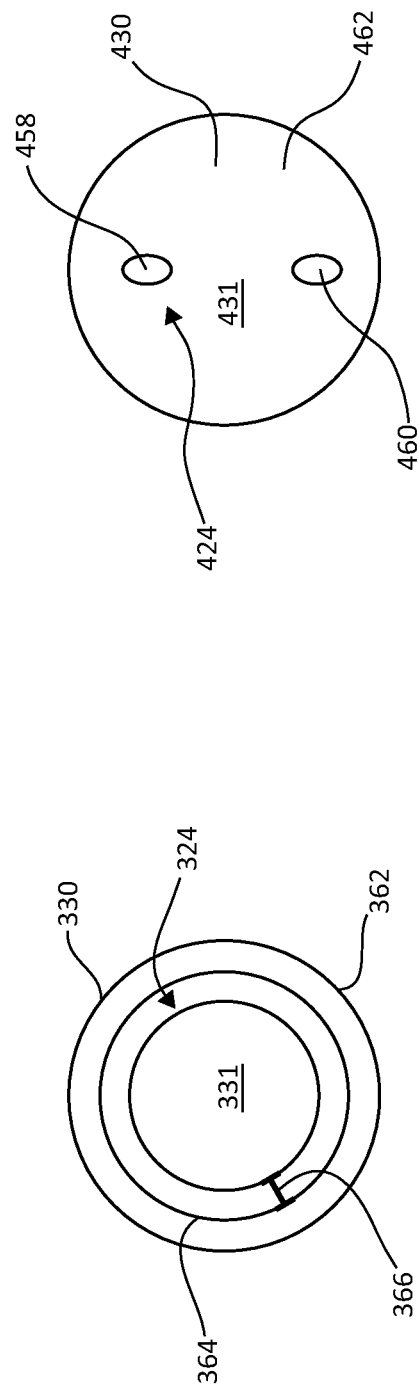

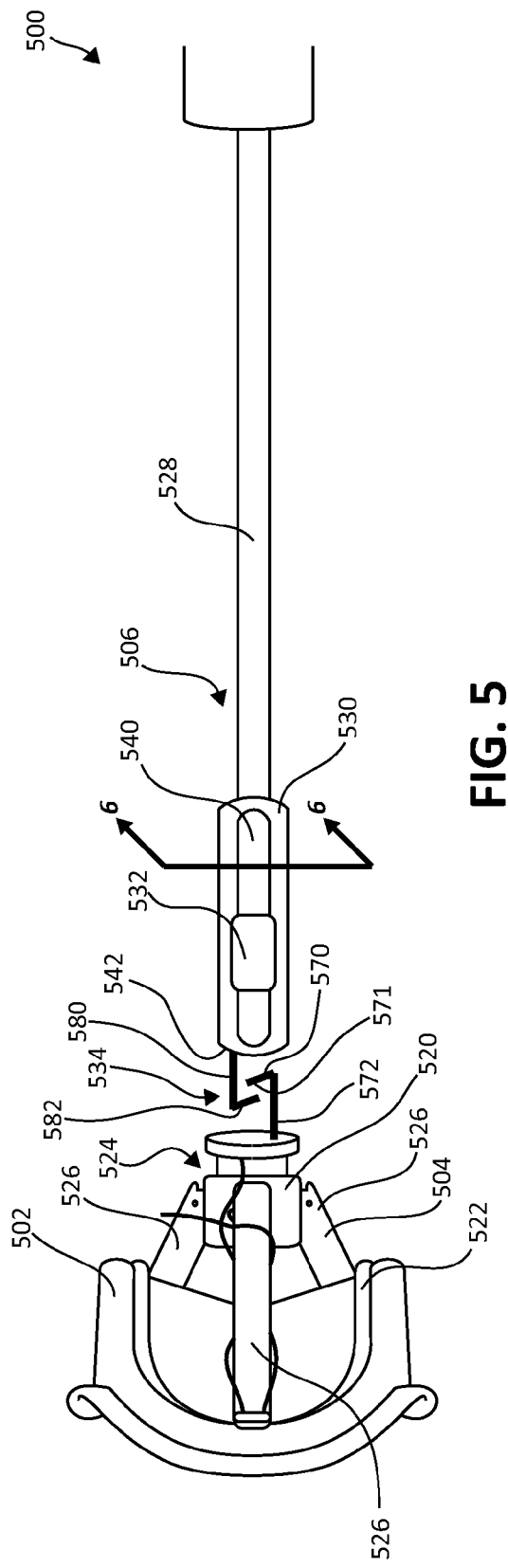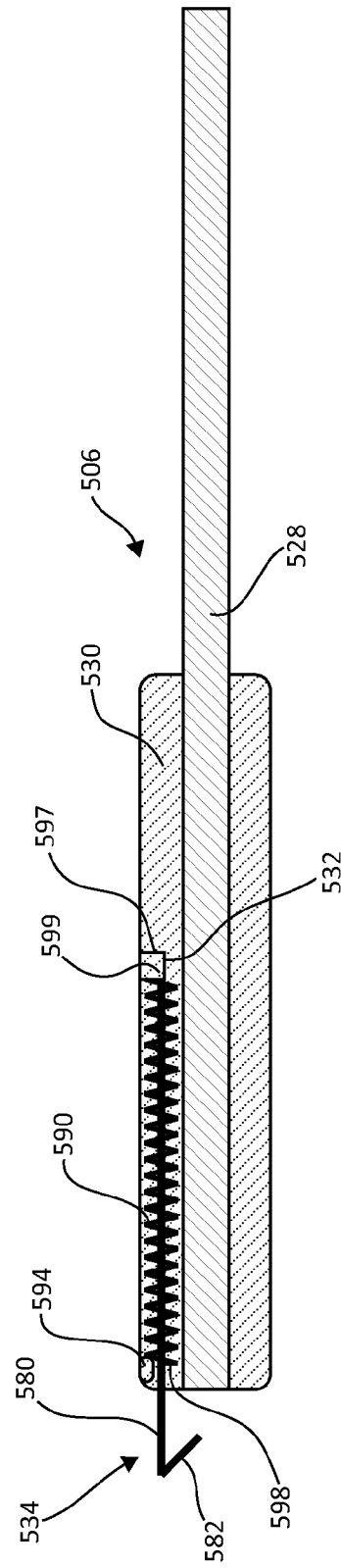

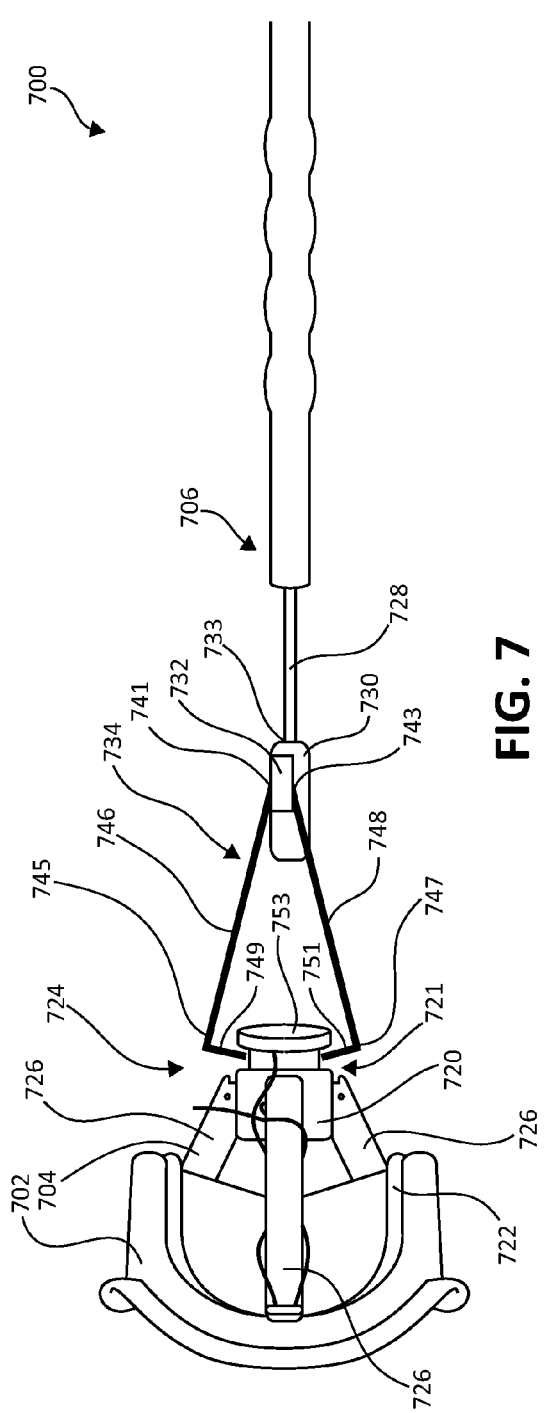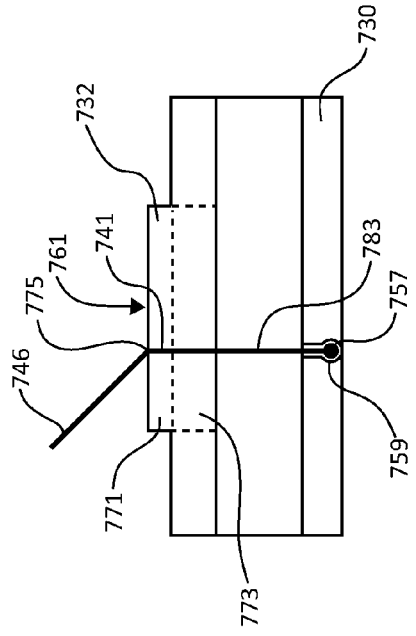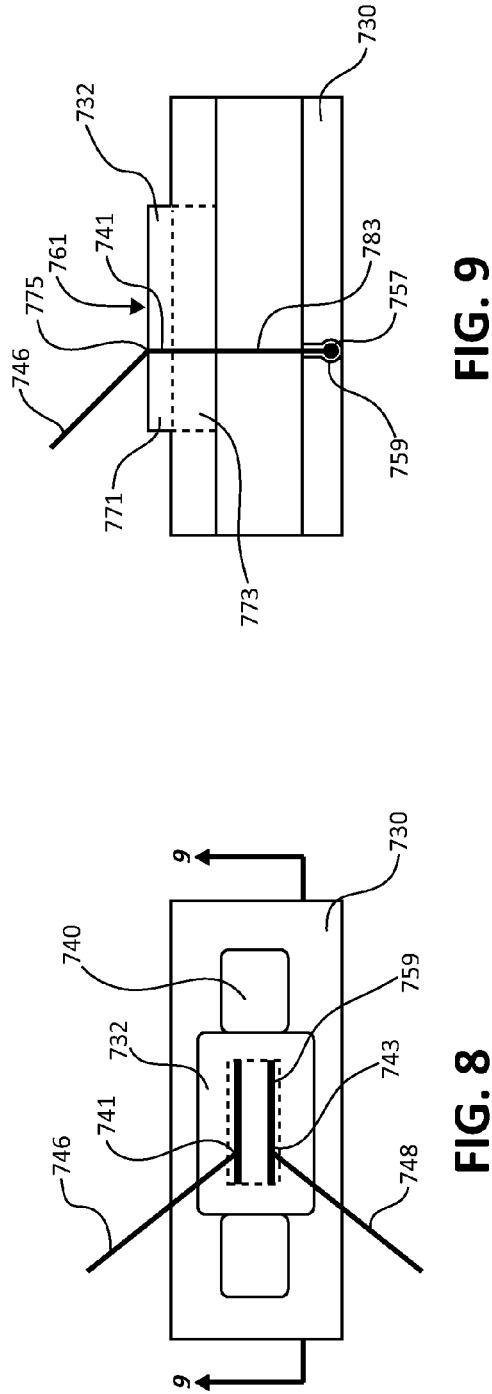

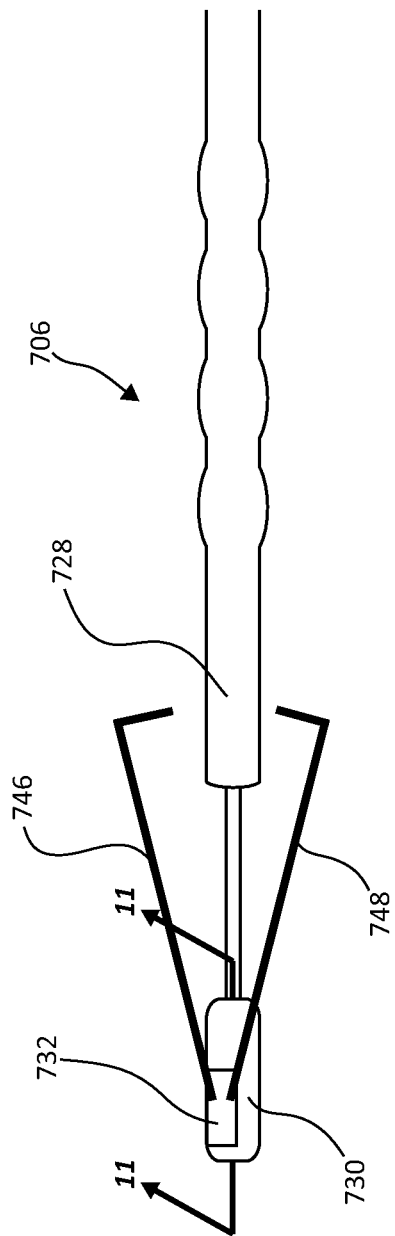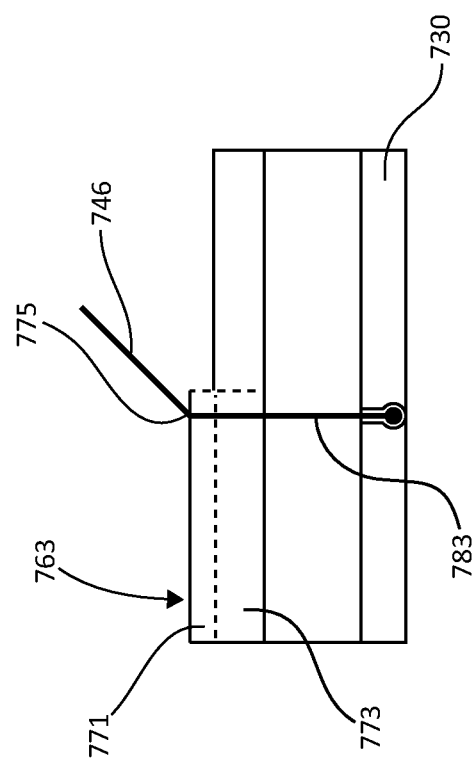

SYSTEMS AND DELIVERY HANDLES FOR DELIVERING PROSTHETIC HEART VALVES DISPOSED ON VALVE HOLDERS

RELATED APPLICATION DATA

The present application claims priority under 35 U.S.C. §119(e) to U.S. Provisional Application No. 61/496,206, filed Jun. 13, 2011.

BACKGROUND

1. Technical Field

The present invention relates in general to prosthetic heart valves, and more particularly, to systems for delivering prosthetic valves.

2. Description of the Related Art

A heart of a mammalian animal is a hollow muscular organ having left and right atria and left and right ventricles, each provided with its own one-way valve. A natural heart includes aortic, mitral (or bicuspid), tricuspid and pulmonary valves, and each valve has leaflets to control a directional flow of blood through the heart. The valves are each supported by an annulus that comprises a dense fibrous ring attached either directly or indirectly to the atrial or ventricular muscle fibers. Over time, the heart (e.g., the valve) may become diseased or damaged. To repair the heart, the valve may undergo a valve replacement operation. In one operation, the damaged leaflets of the valve are excised, and the annulus is sculpted to receive a replacement valve, such as a prosthetic heart valve. Although various types and configurations of prosthetic heart valves for replacing diseased natural human heart valves are known, such valves conventionally comprise a valve and a sewing ring supporting valve leaflets and commissure posts.

Prosthetic heart valves are typically coupled to a valve holder, which aids in the delivery and implantation of the valve into the patient. Due to various factors such as the particular valve to be replaced and the particular configuration of the prosthetic to be implanted, various types of specialized holders have been developed. Generally, valve holders are designed to enable a surgeon to precisely position a prosthetic heart valve within the heart passageway or in another area of the heart. Valve holders are also used to securely hold the prosthetic heart valve in place until suturing is completed and the sutures are tied off.

In the case of implantation of some prosthetic valves, such as a mitral valve, an elongate handle connects to the valve holder. The handle is grasped and manipulated by the surgeon to maneuver the valve to its desired implantation position. The handle is then cut away, and the sewing ring is sutured to the native valve annulus with the valve holder remaining attached to protect the valve.

Although conventional handles are suitable for delivering prosthetic valves to desired locations within a patient, they may be improved. In particular, conventional handles including valve holders attached thereto may obstruct a surgeon's view during a suturing operation. Additionally, conventional handles that are required to be cut away from the valve holder may be difficult to maneuver during delivery and/or suturing.

BRIEF SUMMARY

In an embodiment, by way of example only, a system is provided for delivering a prosthetic heart valve. The system includes a delivery handle, a heart valve, and a valve holder. The delivery handle includes a rod, a button, and a valve holder attachment interface, where the button is configured to move between a first position and a second position along an axial length of the rod, and the valve holder attachment interface is mechanically coupled to the button and configured to move between an engaged position and a disengaged position. The heart valve includes a prosthetic valve. The valve holder is connected to a proximal end of the heart valve and includes a boss, a holder ring, and a handle attachment interface. The holder ring includes the heart valve mounted thereto and is coupled to the boss, and the handle attachment interface is formed on the boss and is configured to receive and mate with the valve holder attachment interface. When the button is in the first position, the valve holder attachment interface is in the engaged position to mechanically couple to the handle attachment interface. When the button is moved to the second position, the valve holder attachment interface moves correspondingly to the disengage position to mechanically release from the handle attachment interface.

In another embodiment, a delivery handle is provided for delivering a prosthetic heart valve disposed on a valve holder. The delivery handle includes a rod, a button, and at least two prongs. The shaft is disposed on a distal end of the rod and having an axial slit. The button extends through the axial slit and is configured to move along a portion of a length of the axial slit between a first position and a second position, the button including a slot. Each of the at least two prongs has a stem extending from a proximal end of each prong. The stem extends through the slot of the button and is rotationally coupled to the shaft to provide a pivot point. When the button is in the first position, the at least two prongs are in a contracted position for mechanically coupling to the valve holder. When the button is moved to the second position, the at least two prongs rotate at the pivot point on the shaft to an expanded position to mechanically release from the valve holder.

In still another embodiment, a delivery handle is provided for delivering a prosthetic heart valve disposed on a valve holder. The delivery handle includes a rod, a hollow shaft through which the rod extends having an axial length and a slit along a portion of the axial length, a valve holder attachment interface comprising a stem and a hook, the stem disposed between the rod and the hollow shaft, and the hook extending at least partially outside of the shaft, and a button coupled to the stem and extending out of the slit of the hollow shaft and configured to move along the axial length of the rod from a first position to a second position. When the button is in the first position, the hook is disposed in a retracted position to mechanically engage an attachment interface on the valve holder. When the button is in the second position, the hook is in a lengthened position to mechanically release from the attachment interface on the valve holder.

In still yet another embodiment, a delivery handle is provided for delivering a prosthetic heart valve disposed on a valve holder. The delivery handle includes a rod, a hollow shaft through which the rod extends having an axial length and a slit extending along a portion of the axial length, a valve holder attachment interface including a cylinder and at least two prongs, the cylinder disposed between the rod and the hollow shaft, and the at least two prongs spaced apart and extending from the cylinder and configured to expand and contract relative to each other, and a button coupled to a portion of the cylinder and extending through the slit to slidably move from a first position to a second position. When the button is in the first position, the at least two prongs expand relative to each other to mechanically couple to an attachment interface on the valve holder. When the button is in the second position, the at least two prongs contract relative to each other to mechanically release from the attachment interface on the valve holder.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 2 is a cross section of a delivery handle for use with the system depicted in FIG. 1 taken along line 2-2, according to an embodiment;

FIG. 3 is an end view of a boss of a valve holder for use with a system for delivering a prosthetic heart valve, according to an embodiment;

FIG. 4 is an end view of a valve holder for use with a system for delivering a prosthetic heart valve, according to another embodiment;

FIG. 5 is a side view of a system for delivering a prosthetic heart valve, according to another embodiment;

FIG. 6 is a cross section of a delivery handle for use with the system depicted in FIG. 5 taken along line 6-6, according to an embodiment;

FIG. 7 is a side view of a system for delivering a prosthetic heart valve including a delivery handle in an engaged position, according to still another embodiment;

FIG. 8 is a close-up view of a shaft, a button, and prongs illustrated in FIG. 7, according to an embodiment;

FIG. 9 is a cross section of the shaft, button, and a prong of FIG. 8 taken along line 9-9, according to an embodiment;

FIG. 10 is a side view of the delivery handle depicted in FIG. 7 in a disengaged position, according to an embodiment; and FIG. 11 is a cross section of the shaft, button, and prong of FIG. 10 taken along line 10-10, according to an embodiment.

DETAILED DESCRIPTION OF THE DRAWINGS

Figure 1:
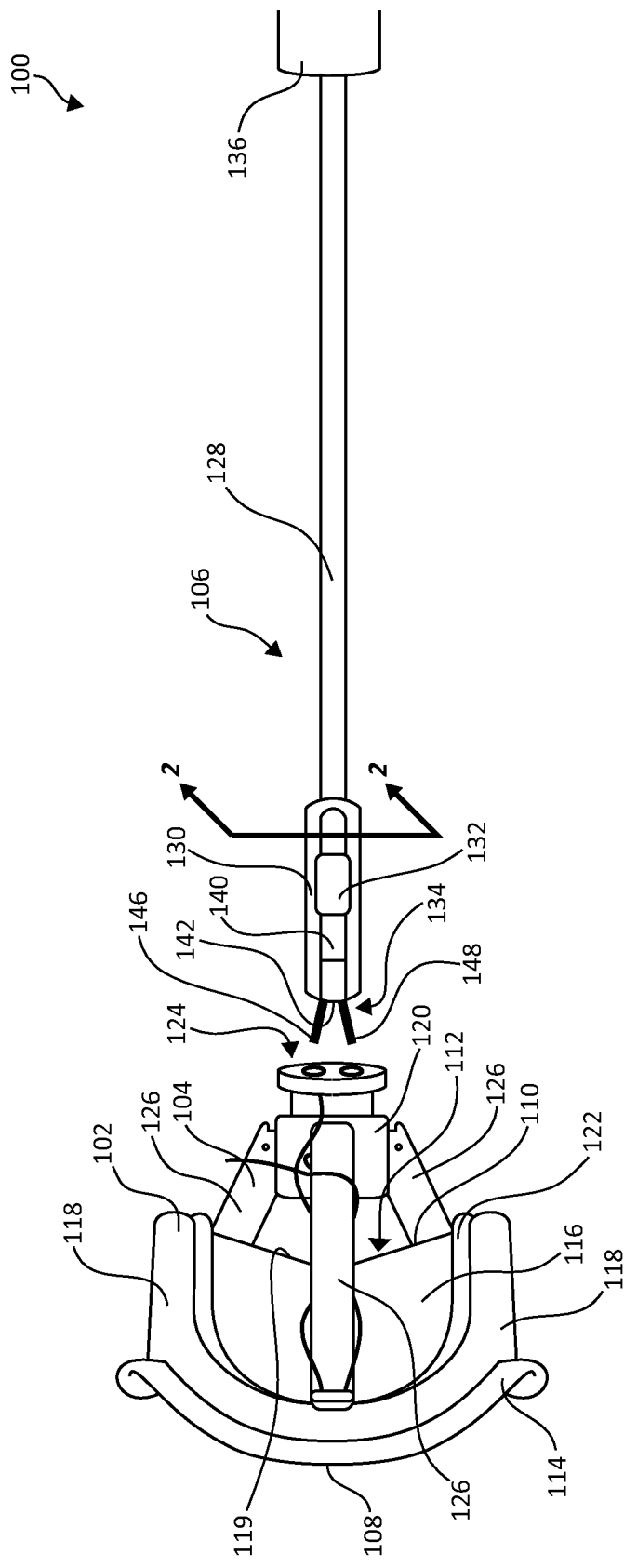
FIG. 1 is a side view of a system for delivering a prosthetic heart valve, according to an embodiment.

The following detailed description is merely exemplary in nature and is not intended to limit the inventive subject matter or the application and uses of the inventive subject matter. Furthermore, there is no intention to be bound by any theory presented in the preceding background or the following detailed description.

A system for delivering a prosthetic heart valve has been provided that is improved over conventional valve delivery systems. The system can be employed in the implantation of an aortic heart valve, a mitral valve or any other valve or valve-type tissue. The system includes a delivery handle that allows a surgeon to release the handle relatively quickly from the prosthetic heart valve with minimal effort, as compared to conventional delivery handles. Generally, the delivery handle includes a rod, a button, and a valve holder attachment interface. The button is configured to move between a first position and a second position along an axial length of the rod. The valve holder attachment interface mechanically couples to the button and is configured to move between an engaged position and a disengaged position. When the button is in the first position, the valve holder attachment interface is in the engaged position to mechanically couple to a handle attachment interface of a valve holder. When the button is moved to the second position, the valve holder attachment moves correspondingly to the disengage position to mechanically release from the handle attachment interface of the valve holder.

FIG. 1 is a side view of a system 100 for delivering a prosthetic heart valve 102, according to an embodiment. The system 100 includes a valve holder 104 and a delivery handle 106. The prosthetic valve 102, depicted here as an aortic valve, is mounted to the valve holder 104 and has an inflow end 108, an outflow end 110, and a flow channel 112 extending therebetween. The inflow end 108 serves as a leading end of the valve 102 during implantation. An annular sewing ring 114 is disposed on the inflow end 108 and is provided for attaching the valve 102 to a desired location within a patient's heart. The sewing ring 114 can be pre-threaded with an array of implant sutures (not shown), in an embodiment. In another embodiment, the sewing ring 114 does not include sutures, but is configured to have a suitable thickness to receive sutures threaded in the patient's heart for securing the prosthetic valve to a tissue making up a valve annulus (e.g., an aortic annulus, a mitral annulus, a tricuspid annulus).

The outflow end 110 includes a plurality of leaflets 116 (only one of which is shown) and a plurality of commissure posts 118 arranged around a central orifice 119. The leaflets 116 comprise flexible material suitable for providing occluding surfaces of the valve 102. For example, the flexible material can be formed from bovine pericardium, porcine valve material or another biocompatible flexible material. In addition, the leaflets 116 may be formed from a xenograft, a homograft or another tissue graft. Although one leaflet 116 is illustrated in FIG. 1, more leaflets 116 can be included in other embodiments.

The plurality of commissure posts 118 extend axially toward the outflow end 110 of the valve 102 so that the commissure posts 118 project distally toward the outflow side of the valve 102. Generally, two of the commissure posts 118 support a leaflet 116, which extends therebetween. Additionally, the commissure posts 118 are circumferentially-spaced around the outflow end 110 of the valve 102. In an embodiment, the commissure posts 118 are substantially evenly spaced around the outflow end 110 of the valve 102. The number of commissure posts 118 included in the valve 102 corresponds to the total number of leaflets 116. The commissure posts 118 are typically less flexible than the leaflets 116. It should be noted that other internal constructions of heart valves having movable commissure posts alternatively can be employed. In other embodiments, the prosthetic valve 102 may include metallic or plastic stent elements, a silicone or urethane insert for the sewing ring 114, biocompatible fabric (i.e., polyester) covering around one or more of the elements or other additional features. Exemplary heart valves are the Carpentier-Edwards porcine and pericardial bioprostheses, sold by Edwards Lifesciences Corp. of Irvine, Calif., and the like.

The prosthetic valve 102 is mounted on the holder 104. In particular, the holder 104 is inserted at least partially into the flow channel 112 of the valve 102 and provides improved visibility to the leaflets 116 during implantation. The holder 104 includes a boss 120, a holder ring 122, and a handle attachment interface 124. The boss 120 is generally cylindrical and can have a solid configuration or a hollow configuration. According to an embodiment, the boss 120 comprises a biocompatible plastic, such as Delrin® material (available through E.I. du Pont de Nemours of Delaware). Another suitable material includes, but is not limited to, polysulfone.

In an embodiment, an outermost diameter of the boss 120 has a measurement in a range of about 1.0 cm to about 3.0 cm and an axial length in a range of about 0.6 cm to about 1.0 cm. In other embodiments, the dimensions of the boss 120 are greater or less than the aforementioned ranges.

The holder ring 122 is configured to comprise the structure of the valve holder 104 to which the prosthetic valve 102 can be mounted. In this regard, the holder ring 122 has an outer diameter that is substantially equal (e.g., ±0.5 mm) to a diameter of the prosthetic valve flow channel 112. In an embodiment, the holder ring 122 is disposed concentric to the boss 120 and can be located downstream from the boss 120. The holder ring 122 comprises a biocompatible plastic, such as Delrin® material (available through E.I. du Pont de Nemours of Delaware). Another suitable material includes, but is not limited to, polysulfone.

The boss 120 and the holder ring 122 can be coupled to each other by a plurality of arms 126. Although three arms are shown in FIG. 1, it will be appreciated that more or fewer arms 126 can be included in other embodiments. The plurality of arms 126 can comprise a biocompatible plastic, such as Delrin® material (available through E.I. du Pont de Nemours of Delaware), polysulfone or another suitable material. In accordance with an embodiment, the arms 126 comprise a material that is substantially similar to that of the boss 120 and/or the holder ring 122. In another embodiment, the arms 126 comprise a different material than the boss 120 and/or the holder ring 122. The handle attachment interface 124 is formed on the boss 120 and is configured to receive and engage with the delivery handle 106.

As alluded to previously, the delivery handle 106 can be temporarily coupled to the valve holder 104 and is configured to allow the surgeon to position the prosthetic valve 102 in a desired location within the patient. In this regard, the delivery handle 106 includes a rod 128, a shaft 130, a button 132, and a valve holder attachment interface 134. The rod 128 is configured to provide a grip 136 to allow the surgeon to manipulate the delivery handle 106. In an embodiment, the rod 128 has a length in a range of about 7.0 cm to about 15.0 cm. In other embodiments, the rod 128 is longer or shorter than the aforementioned range. In an embodiment, the rod 126 comprises a medical grade stainless steel. Suitable materials include, but are not limited to stainless steel (SS 304), nitinol, and aluminum.

The rod 128 and the grip 136 comprise substantially similar material, in an embodiment. In another embodiment, the rod 128 and the grip 136 are integrally formed from a single material. In another embodiment, different materials form the rod 128 and the grip 136. In such case, the grip 136 can comprise a biocompatible plastic, such as Radel® RS100 (available through Westlake Plastics Company of Lenni, Pa.), Delrin® or another suitable material.

The shaft 130 is hollow and is mounted to the rod 128. In an embodiment, the shaft 130 extends along a portion of the length of the rod 128. For example, the shaft 130 has an axial length in a range of about 2.5 cm to about 5.0 cm. In another embodiment, the axial length is longer or shorter than the aforementioned range. A slit 140 extends along a portion of the axial length of the shaft 130. In an embodiment, the slit 140 is configured to receive a portion of the button 132 to thereby allow the button 132 to move, in this example slide, from position to position along the axial length. In an embodiment, the shaft 130 can comprise a biocompatible plastic, such as Radel® RS100 (available through Westlake Plastics Company of Lenni, Pa.), Delrin® or another suitable material.

The button 132 is configured to provide a grip for the surgeon during handle manipulation. For example, the button 132 can be hemispherical, rectangular or another shape suitable for gripping. In an embodiment, the button 132 has a surface finish that improves frictional contact. In this regard, the button 132 can have one or more roughened outer surfaces, in an embodiment. In another embodiment, the button 132 has one or more surfaces that include a non-slip lining. In other embodiments, the button 132 has a smooth outer surface and a shape that is conducive for providing the improved grip.

The valve holder attachment interface 134 extends away from a distal end 142 of the rod 128. As will be discussed in greater detail below, the valve holder attachment interface 134 is coupled to the button 132 so that when the button 132 is in a first position on the shaft 130, the valve holder attachment interface 134 is in an engaged position and is ready to mechanically couple to the handle attachment interface 124. When the button 132 is moved to a second position, the valve holder attachment interface 134 moves correspondingly with the button 132 to a disengaged position to mechanically release itself from the handle attachment interface 124.

FIG. 2 is a cross section of the delivery handle 106 for use with system 100 of FIG. 1 along line 2-2, according to an embodiment. The valve holder attachment interface 134 includes a cylinder 144 and two or more prongs 146, 148. The cylinder 144 can be coupled to the button 132 (FIG. 1) and is configured to be slidably disposed between the shaft 130 and the rod 128. In this regard, a clearance 150 is provided between an inner surface 152 of the shaft 130 and an outer surface 154 of the rod 128 to allow the valve holder attachment interface 134 to be disposed therebetween. In an example, the clearance 150 is a distance in a range of about 0.2 cm to about 0.5 cm. In other embodiments, the clearance 150 is greater or less than the aforementioned range.

The two or more prongs 146, 148 extend from the cylinder 144 and are configured to form a friction fit with the handle attachment interface 124. In an example, the prongs 146, 148 comprise wires that are angled away from each other. The prongs 146, 148 have a length in a range of about 1.0 cm to about 2.5 cm. In another embodiment, the prongs 146, 148 can be longer or shorter than the aforementioned range.

The wires comprising the prongs 146, 148 are formed from biocompatible spring material. Examples of suitable materials from which the wires can be formed include, but are not limited to nitinol. In this way, the prongs 146, 148 can be temporarily deformed and angled toward each other for insertion into the handle attachment interface 124. When the prongs 146, 148 are disposed within the handle attachment interface 124, the prongs 146, 148 relax and resume a natural shape to provide the friction fit against the handle attachment interface 124. When the button 132 is slid in a direction 161 along the rod 128, the prongs 146, 148 move into the clearance 150 and contact the inner surface 152 of the shaft 130, which forces the distal ends of the prongs 146, 148 to move toward each other to thereby release from the handle attachment interface 124.

FIG. 3 is an end view of a boss 330 of a valve holder (e.g., valve holder 104 of FIG. 1) for use with a system for delivering a prosthetic heart valve, according to an embodiment. The boss 330 includes a main body 362 and a handle attachment interface 324. In an embodiment, the handle attachment interface 324 is configured to engage with the valve holder attachment interface 134 (FIGS. 1 and 2) and is formed in an end surface 331 of the boss 330. In accordance with an example, the handle attachment interface 324 is an annular channel having an outer diameter (e.g. OD 364) that is less than a largest distance between the prongs 146, 148 (FIGS. 1 and 2) and a width 366 and a depth (not shown) suitable for accommodating the prongs 146, 148. For example, the OD 364 of the annular channel can be in a range of about 5.0 mm to about 15.0 mm, the width 366 of the annular channel can be in a range of about 1.0 mm to about 3.0 mm, and the depth can be in a range of about 3.0 mm to about 7.0 mm. In other embodiments, one or more of the OD, the width, and/or the depth may be greater or less than the aforementioned ranges.

FIG. 4 is an end view of a boss 430 of a valve holder (e.g., valve holder 104 of FIG. 1) for use with a system for delivering a prosthetic heart valve, according to another embodiment. The boss 430 includes a main body 462 and a handle attachment interface 424. The handle attachment interface 424 formed on an end surface 431 of the boss 430 is configured to mate and/or engage with the valve holder attachment interface (e.g., valve holder attachment interface 134 of FIG. 1). In an embodiment, the handle attachment interface 424 comprises a plurality of openings 458, 460 suitably dimensioned and arranged on the boss 430 for accommodating the prongs (e.g., prongs 146, 148 of FIG. 1). Although two openings 458, 460 are illustrated in FIG. 4, more or fewer may be included depending on a total number of prongs 146, 148.

FIG. 5 is a side view of a system 500 for delivering a prosthetic heart valve 502, according to another embodiment. The system 500 includes a valve holder 504 and a delivery handle 506 to which the prosthetic valve 502 is mounted. The prosthetic valve 502 is configured substantially similar to prosthetic valve 102 in FIG. 1. The valve holder 504 includes a boss 520, a holder ring 522, and a plurality of arms 526 that are configured similar to boss 120, holder ring 122, and plurality of arms 126 of FIG. 1, except a handle attachment interface 524 of the boss 520 comprises a hook 570 and a stem 572. The hook 570 and stem 572 can comprise a bio compatible metal material. Suitable materials include, but are not limited to nitinol, stainless steel, and aluminum. In an embodiment, the hook 570 and stem 572 are integrally formed from the same material. In another embodiment, the hook 570 and stem 572 are separate pieces that are coupled together. In still another embodiment, the hook 570 and stem 572 comprise the same material and/or are integrally formed with the boss 520.

In any case, the stem 572 extends from the boss 520. In accordance with an embodiment, the stem 572 is coupled to the boss 520 and has a first portion embedded in the boss 520. The hook 570 is v-shaped, in an embodiment. In another embodiment, the hook 570 is curved. Preferably, an end 571 of the hook 570 is blunt or smooth to prevent puncturing the prosthetic valve or other tissue that may come into contact with the hook 570.

The delivery handle 506 is configured to correspond with the handle attachment interface 524 and includes a rod 528, a shaft 530, a button 532, and a valve holder attachment interface 534. The rod 528 and shaft 530 are configured similar to rod 128 and shaft 130 illustrated in FIG. 1. For example, the shaft 530 includes a slit 540 configured to receive a portion of the button 532 to thereby allow the button 532 to move from position to position along the axial length.

The valve holder attachment interface 534 extends from a distal end 542 of the rod 528 and comprises a stem 580 and a hook 582. The stem 580 and hook 582 can comprise a biocompatible metal material. Suitable materials include, but are not limited to nitinol, stainless steel, and aluminum. In an embodiment, the stem 580 and hook 582 are integrally formed from the same material. In another embodiment, the stem 580 and hook 582 are separate pieces that are coupled together. The hook 582 can be v-shaped, curved or have another shape. Preferably, an end of the hook 582 is blunt or smooth to prevent puncturing the prosthetic valve or other tissue that may come into contact with the hook 582.

FIG. 6 is a cross section of one embodiment of the delivery handle 506 for use in the system 500 depicted in FIG. 5 taken along line 6-6. In an embodiment, the stem 580 is attached to the button 532 so that when the button is in a first position on the shaft 530, the hook 582 of the valve holder attachment interface 534 is in an engaged (i.e., retracted) position to mechanically couple to the hook 570 of the handle attachment interface 524. When the button 532 is moved to a second position, the hook 582 of the valve holder attachment interface 534 moves correspondingly with the button 532 to a disengaged (i.e., lengthened) position to mechanically release itself from the hook 570 of the handle attachment interface 542.

To provide tension when the valve holder attachment interface 534 is in the engaged position, a spring 590 is provided. The spring 590 is disposed between the rod 528 and the shaft 530 and extends between the button 532 (FIG. 5) and the hook 582 of the valve holder attachment interface 534. In an embodiment, the shaft 530 has a radially inward flange 594 against which an end 598 of the spring 590 abuts. An opposite end 599 of the spring 590 is disposed against an attachment portion 597 of the button 532. In other embodiments, the spring 590 is mounted between the hook 582 of the valve holder attachment interface 534 and button 530.

FIG. 7 is a side view of a system 700 for delivering a prosthetic heart valve 702 according to still another embodiment. The system 700 includes a valve holder 704 and a delivery handle 706 to which the prosthetic valve 702 is mounted. The prosthetic valve 702 is configured substantially similar to prosthetic valve 102 in FIG. 1. The valve holder 704 includes a boss 720, a holder ring 722, and a plurality of arms 726 that are configured similar to boss 120, holder ring 122, and plurality of arms 126 of FIG. 1, except a handle attachment interface 724 of the boss 720 comprises one or more outer diameter channels 721 (only one of which is shown in FIG. 7).

In an embodiment, the one or more outer diameter channels 721 extend radially around an outer surface of the boss 720. For example, the outer diameter channel 721 extends partially around an outer diameter of the boss 720. In another example, more than one outer diameter channel is included, and the channels are spaced apart around the outer diameter of the boss 720 to correspond with a valve holder attachment interface 734 of the delivery handle 706. In still another embodiment, the outer diameter channel 721 extends completely around the outer diameter of the boss 720.

The one or more outer diameter channels 721 can form openings through the boss 720. According to an embodiment, the channels 721 extend partially through the boss 720 to have a depth. The depth is in a range of about 0.3 cm to about 0.8 cm. In another embodiment the depth is greater or less than the aforementioned range. In embodiments in which more than one channels 721 are included, the depths of two or more of the channels 721 may vary. In any case, the outer diameter channel 721 is configured to engage with a valve holder attachment interface 734 of the delivery handle 706 when in an engaged (i.e., contracted) position, as shown in FIG. 7.

The delivery handle 706 includes a rod 728, a button 732, and the valve holder attachment interface 734. The rod 728 is configured similar to rod 128 illustrated in FIG. 1, except the rod 728 has a shaft 730 on its distal end 733. The button 732 is slidably mounted to the shaft 730 to move along the axial length of the shaft 730. In an embodiment, the shaft 730 has an outer diameter in a range of about 0.7 cm to about 1.5 cm. In another embodiment, the diameter of the shaft 730 is wider or narrower than the aforementioned range. According to an embodiment, the shaft 730 is a separate component that is coupled to the distal end 733 of the rod 728. In such case, the shaft 730 comprises a medical grade plastic material such as Delrin®. Other suitable materials include medical grade metals including but not limited to, stainless steel and aluminum. In another embodiment, the shaft 730 is integrally formed as part of the rod 728.

The valve holder attachment interface 734 comprises two or more prongs 746, 748. In an embodiment, each prong 746, 748 has a proximal end 741, 743 a distal end 745, 747, and a tooth 749, 751. The proximal ends 741, 743 of the prongs 746, 748 extend through the button 732. The teeth 749, 751 extend from the distal ends 745, 747 toward each other. Although two prongs 746, 748 are depicted in FIG. 7, more prongs are included in other embodiments. The prongs 746, 748 comprise medical grade spring material, such as nitinol, stainless steel or aluminum. In other embodiments, the prongs 746, 748 comprise other biocompatible material.

The prongs 746, 748 are spaced a distance apart from each other on the button 732. According to an embodiment, the prongs 746, 748 have a length in a range of about 3.0 cm to about 5.0 cm. In other embodiments, the prongs 746, 748 are longer or shorter than the aforementioned range. In an embodiment, a portion of each of the prongs 746, 748 including the teeth 749, 751 extend a distance past a distal end of the shaft 730 when the prongs 746, 748 are in the contracted position. The distance is greater than a length from the outer diameter channel 721 of the boss 720 to a proximal end 753 of the boss 720.

FIG. 8 is a close-up view of the shaft 730, button 732, and prongs 746, 748 shown in FIG. 7, according to an embodiment, and FIG. 9 is a cross section of the shaft 730, button 732, and prong 746 of FIG. 8 taken along line 9-9, according to an embodiment. With reference to FIGS. 7-9, the proximal ends 741, 743 of the prongs 746, 748 are rotationally attached to the shaft 730. Specifically, each prong 746, 748 includes a stem 783 (only one of which is shown in FIG. 9) extending through a slot 759 formed in the button 732, where the stem 783 rotationally attaches to the shaft 730. In an embodiment, the stem 783 is rotationally attached to the shaft 730 to provide a pivot point 775. For example, the stem 783 can include a ball 757 disposed in a suitably-configured cavity 759 formed in the shaft 730 or can include another mechanism to provide rotational movement of the prong 746, 748 relative to the shaft 730.

The stem 783 and its corresponding prong 746, 748 are angled relative to each other. Rotation of the stem 783 causes the proximal end 741, 743 of the prong 746, 748 including the tooth 749, 751 to rotate as well. It will be appreciated that the particular angle at which the stem 783 and corresponding prong 746, 748 are disposed depends on factors such as a length of the prong 746, 748 and a distance between the teeth 749, 751 of the prongs 746, 748.

The slot 759 provides a guide for the prongs 746, 748. In particular, as the button 732 is moved, the walls defining the slot 759 provide friction against the prongs 746, 748 to thereby cause the prongs 746, 748 to rotate. In this regard, the walls defining the slot 759 can include a surface designed to grip and improve the frictional contact with the prongs 746, 748, in an embodiment. In another embodiment, the walls can include a brush attachment. In still another embodiment, the walls defining the slot 759 include a non-slip lining. In any case, the slot 759 extends at least partially along a length of the button 732. In an embodiment, two slots 759 are included (as shown in FIG. 8). In another embodiment, as shown in phantom in FIG. 8, a single slot 759 is formed in the button 732.

The button 732 extends through an axial slit 740 in the shaft 730 and includes a portion 771 that resides outside of the shaft 730 and a second portion 773 (shown in phantom) disposed in the shaft 730. To maintain the button 732 coupled to the shaft 730, the axial slit 740 has a width that is less than the length and width of the portions 771, 773 of the button 732. During operation, when the button 730 is disposed in the first position 761, the prongs 746, 748 are in an engaged (i.e., contracted) position for mechanically coupling to the valve holder 704.

FIG. 10 is a side view of the delivery handle 706 depicted in FIG. 7 in a disengaged (i.e., expanded) position, according to an embodiment, and FIG. 11 is a cross section view of the shaft 730, button 732, and prong 746 of FIG. 10 taken along line 11-11, according to an embodiment. As shown in FIGS. 10 and 11, when the button 730 is moved to the second position 763, the prongs 746, 748 rotate at the pivot point 775 on the shaft 730 to a disengaged (i.e., expanded) position, which causes the prongs 746, 748 to mechanically release from the valve holder (e.g., valve holder 704). Specifically, the teeth 749, 751 on the prongs 746, 748 are rotated to a position toward a proximal end of the rod 728.

By including the valve holder attachment interface and the button for mechanically manipulating the valve holder attachment interface, the handle can be detached from the valve holder with minimal effort. Additionally, the quick release of the delivery handle from the valve holder, as compared to conventional release mechanisms, can improve a surgeon's view of a treatment area in a patient. Moreover, as previously noted, although the system for delivering the prosthetic valve can be used with aortic valves as described above, the system alternatively can be used for implanting mitral valves. In such case, the outflow end of the prosthetic valve serves as a leading end during implantation. Accordingly, the delivery handle interface extends out of the inflow end of the prosthetic valve, to couple with the valve holder attachment interface.

While at least one exemplary embodiment has been presented in the foregoing detailed description of the inventive subject matter, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the inventive subject matter. It being understood that various changes may be made in the function and arrangement of elements described in an exemplary embodiment without departing from the scope of the inventive subject matter as set forth in the appended claims.

What is claimed is:

1. A system for delivering a prosthetic heart valve comprising:
a delivery handle including a rod, a button, and a valve holder attachment interface, the button configured to move between a first position and a second position along an axial length of the rod, and the valve holder attachment interface mechanically coupled to the button and configured to move between an engaged position and a disengaged position, a shaft mounted on a portion of the rod the rod extending through the shaft, the shaft includes an axial length and a slit extending along a portion of the axial length;
a prosthetic heart valve; and a valve holder coupled to the heart valve, the valve holder including a boss, a holder ring, and a handle attachment interface, the holder ring including the heart valve mounted thereto and coupled to the boss, and the handle attachment interface formed on the boss and configured to receive and mate with the valve holder attachment interface, wherein:

when the button is in the first position, the valve holder attachment interface is in the engaged position to mechanically couple to the handle attachment interface, and when the button is moved to the second position, the valve holder attachment interface moves correspondingly to the disengaged position to mechanically release from the handle attachment interface, wherein the valve holder attachment interface comprises at least two prongs spaced apart and configured to contract relative to each other when the button is in the first position and to expand relative to each other when the button is in the second position, and the valve holder attachment interface includes a cylinder from which the at least two prongs extend that is disposed between the rod and the shaft, and the button is coupled to a portion of the cylinder and extends through the slit.

2. The system of claim 1, wherein the handle attachment interface includes a channel configured to receive the at least two prongs.

3. The system of claim 2, wherein the channel comprises an annular channel.

4. The system of claim 2, wherein the handle attachment interface includes at least two channels corresponding with and configured to receive the at least two prongs.

5. The system of claim 2, wherein the channel is formed on an outer diameter of the boss.

6. The system of claim 2, wherein the channel is formed on an end of the boss.

7. A system for delivering a prosthetic heart valve comprising:
a delivery handle including;
a rod;
a hollow shaft mounted on a distal portion of the rod and through which the rod extends having an axial length and a slit extending along a portion of the axial length;
a valve holder attachment interface including a cylinder and at least two prongs, the cylinder disposed between the rod and the hollow shaft, and the at least two prongs spaced apart and extending from the cylinder and configured to expand and contract relative to each other; and a button coupled to a portion of the cylinder and extending through the slit to move from a first position to a second position, wherein:
a prosthetic heart valve;
a valve holder coupled to the heart valve including a handle attachment interface configured to receive and mate with the valve holder attachment interface;
when the button is in the first position, the at least two prongs expand relative to each other to mechanically couple to an attachment interface on the valve holder, and when the button is in the second position, the at least two prongs contract relative to each other to mechanically release from the attachment interface on the valve holder.

8. The delivery handle of claim 7, wherein the at least two prongs are configured to be angled away from each other when expanded.

9. The delivery handle of claim 7, wherein the at least two prongs comprise a biocompatible spring material.

10. A system for delivering a prosthetic heart valve comprising:
a delivery handle including a rod, a button, and a valve holder attachment interface, the button configured to move between a first position and a second position along an axial length of the rod, and the valve holder attachment interface mechanically coupled to the button and configured to move between an engaged position and a disengaged position;
a prosthetic heart valve; and
a valve holder coupled to the heart valve, the valve holder including a boss, a holder ring, and a handle attachment interface, the holder ring including the heart valve mounted thereto and coupled to the boss, and the handle attachment interface formed on the boss and configured to receive and mate with the valve holder attachment interface, wherein:
when the button is in the first position, the valve holder attachment interface is in the engaged position to mechanically couple to the handle attachment interface, and when the button is moved to the second position, the valve holder attachment interface moves correspondingly to the disengage position to mechanically release from the handle attachment interface, wherein the valve holder attachment interface comprises at least two prongs spaced apart and configured to contract relative to each other when the button is in the first position and to expand relative to each other when the button is in the second position;
a shaft disposed on a distal end of the rod, the shaft having an axial slit, the rod extending through the shaft, the button slidably mounted to the shaft through the axial slit, configured to slide along a portion of a length of the axial slit between the first position and the second position, and including a slot, and at least two prongs each having a stem extending from a proximal end of each prong, the stem extending through the slot of the button and rotationally coupled to the shaft to provide a pivot point, wherein:
when the button is in the first position, the at least two prongs are in a contracted position for mechanically coupling to the valve holder, and when the button is moved to the second position, the at least two prongs rotate at the pivot point on the shaft to an expanded position to mechanically release from the valve holder.

11. The delivery handle of claim 10, wherein: each of the at least two prongs includes a tooth, when the button is in the first position, each tooth extends past a distal end of the shaft to grip the valve holder, and when the button is in the second position, each tooth is released from the valve holder.

12. The system of claim 10, wherein the handle attachment interface includes a channel configured to receive the at least two prongs.

13. The system of claim 12, wherein the channel comprises an annular channel.

14. The system of claim 12, wherein the handle attachment interface includes at least two channels corresponding with and configured to receive the at least two prongs.

15. The system of claim 12, wherein the channel is formed on an outer diameter of the boss.

16. The system of claim 12, wherein the channel is formed on an end of the boss.

* * * * *